(12) United States Patent
Myakishev-Rempel et al.

(10) Patent No.: US 11,944,836 B2
(45) Date of Patent: Apr. 2, 2024

(54) METHOD AND WEARABLE DEVICE TO STIMULATE POSITIVE DNA GENE EXPRESSION AND OTHER POSITIVE BIOLOGICAL PROCESSES AND MITIGATE NEGATIVE DNA GENE EXPRESSION AND OTHER NEGATIVE BIOLOGICAL PROCESSES IN ORDER TO IMPROVE HEALTH AND WELLNESS

(71) Applicants: Max Myakishev-Rempel, San Diego, CA (US); Alexandre Perry Kamel, Centennial, CO (US)

(72) Inventors: Max Myakishev-Rempel, San Diego, CA (US); Alexandre Perry Kamel, Centennial, CO (US)

(73) Assignee: DNA VIBE, LLC, Centennial, CO (US)

( * ) Notice: Subject to any disclaimer, the term of this patent is extended or adjusted under 35 U.S.C. 154(b) by 326 days.

(21) Appl. No.: 17/187,730

(22) Filed: Feb. 26, 2021

(65) Prior Publication Data
US 2021/0308477 A1    Oct. 7, 2021

Related U.S. Application Data

(60) Provisional application No. 63/100,354, filed on Mar. 9, 2020.

(51) Int. Cl.
*A61N 2/00* (2006.01)
*A61B 5/0205* (2006.01)
(Continued)

(52) U.S. Cl.
CPC .............. *A61N 2/002* (2013.01); *A61N 1/40* (2013.01); *A61N 2/02* (2013.01); *A61N 5/06* (2013.01);
(Continued)

(58) Field of Classification Search
CPC . A61B 5/02055; A61B 5/021; A61B 5/02438; A61B 5/4836; A61B 5/6831;
(Continued)

(56) References Cited

U.S. PATENT DOCUMENTS

| | | | |
|---|---|---|---|
| 10,610,696 B1 * | 4/2020 | Peled | A61N 1/403 |
| 2019/0246463 A1 * | 8/2019 | Williams | A61N 5/06 |
| 2019/0329065 A1 * | 10/2019 | Gandel | A61B 18/203 |

FOREIGN PATENT DOCUMENTS

| | | | | |
|---|---|---|---|---|
| ES | 2940792 T3 * | 5/2023 | | A61N 2/00 |
| WO | WO-2021048642 A1 * | 3/2021 | | A61B 5/0004 |

OTHER PUBLICATIONS

DNA vibe—intelligent light therapy—reduce pain & speed recovery. DNAVibe. (Jan. 21, 2021). https://dnavibe.com/ (Year: 2021).*

* cited by examiner

*Primary Examiner* — Christine H Matthews
*Assistant Examiner* — Marc D. Honrath
(74) *Attorney, Agent, or Firm* — Boris Leschinsky

(57) ABSTRACT

This present invention is a novel method and wearable device for stimulating positive DNA gene expression and mitigating negative DNA gene expression in order to improve health and wellness. The invention's unique characteristics include the application of multiple modalities, their unique configuration for safe, low-power application, the wearable device's unique arrangement in a flat, flexible configuration for elastic contouring with comfort required for an extended period of wearing, and the ability to optimize and personalize the parameters and mixing among such modalities. The invention further combines biometric feedback data with Artificial Intelligence analytic capabilities, to facilitate the identification and characterization of DNA resonant frequencies, and associated "stimulus-response" modeling associated with such biological interactions. The (Continued)

present invention will provide unique guidance to discover the optimal input-output parameters to actively control DNA and gene expression with a prescriptive approach to selectively activate certain positive expressions and to selectively suppress certain negative expressions.

22 Claims, 7 Drawing Sheets

(51) Int. Cl.
*A61B 5/021* (2006.01)
*A61N 1/40* (2006.01)
*A61N 2/02* (2006.01)
*A61N 5/06* (2006.01)
*G16H 20/30* (2018.01)
*G16H 40/67* (2018.01)
*A61B 5/00* (2006.01)
*A61B 5/024* (2006.01)

(52) U.S. Cl.
CPC ............ *G16H 20/30* (2018.01); *G16H 40/67* (2018.01); *A61B 5/02055* (2013.01); *A61B 5/021* (2013.01); *A61B 5/02438* (2013.01); *A61B 5/4836* (2013.01); *A61N 2005/0645* (2013.01); *A61N 2005/0652* (2013.01)

(58) Field of Classification Search
CPC . A61N 1/40; A61N 2/002; A61N 2/02; A61N 2005/0645; A61N 2005/0652; A61N 5/06; G16H 20/30; G16H 40/67
See application file for complete search history.

METHOD AND WEARABLE DEVICE TO STIMULATE POSITIVE DNA GENE EXPRESSION AND OTHER POSITIVE BIOLOGICAL PROCESSES AND MITIGATE NEGATIVE DNA GENE EXPRESSION AND OTHER NEGATIVE BIOLOGICAL PROCESSES IN ORDER TO IMPROVE HEALTH AND WELLNESS

CROSS-REFERENCE TO RELATED APPLICATIONS

This application claims priority under 35 U.S.C. § 119(e) to U.S. Provisional Application Ser. No. 63/100,354, titled "A technology, method, and functional product design to stimulate positive (and mitigate negative) DNA gene expression and other biological processes to improve health and wellness," filed on Mar. 9, 2020, which is hereby incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND

Technical Field

Aspects of the present invention relate to the field of consumer products, particularly in the fields of consumer health, wellness, and fitness technology wearables.

More particularly, aspects of the present invention relate to a method and wearable device to stimulate positive DNA gene expression and other positive biological processes and to suppress negative DNA gene expression and other negative biological processes, wherein positive is defined as beneficial for health and wellbeing and negative is defined as detrimental for health and wellbeing.

Discussion of Related Art

It is well understood by those in the field that DNA, and genes in particular, govern protein synthesis and cellular generation, form, and function, and, as such, play a vital role in governing the health and wellbeing of biological systems.

Although many positive genetic and biological mechanisms are known, in many cases, it has been a challenge to harness the benefits of these positive mechanisms to their full extent as there is often no known consistent or optimal method to activate or stimulate such positive mechanisms. Even where a consistent or optimal method is known, it is often difficult to administer the method as its technology is expensive, burdensome, or unportable. The same challenges apply to the deactivation or suppression of negative DNA and genetic mechanisms.

Based on our extensive experience in genomics and biophysical research of the effects of light and electromagnetic waves on biological objects, as evidenced in Myakishev-Rempel, Max, et al. "Red light modulates ultraviolet-induced gene expression in the epidermis of hairless mice." Photomedicine and laser surgery 33.10 (2015): 498-503, gene expression (activity) may be influenced, (stimulated or suppressed) by engaging DNA molecules, cells and tissues with various modes of energies.

Dr. Rempel's observations and research suggest that DNA and genes can be activated or deactivated, and potentially caused to resonate, which further affects such phenomena, when subject to particular patterns of energies. Said patterns include varying the intensity, frequency, waveforms and the like of energies including optical, electromagnetic, magnetic pulse, and the like.

Accordingly, the present invention relates to a method and wearable device for identifying, and using, optimal patterns and parameters of modalities to stimulate positive DNA gene expression and other positive biological processes and to suppress negative DNA gene expression and other negative biological processes. Furthermore, the present invention relates to a wearable device with physiological and biometric sensors as well as modalities that is portable and easily forms to the contours of treatment areas.

SUMMARY

Based on these observations, one aspect of the present invention is a novel wearable device that gently and safely illuminates biological tissues with low levels of various energies to activate or stimulate positive gene expression as a way to promote desired results including accelerated healing, pain relief, and performance enhancement through the generation of healthy tissue cells. Through a similar process, alternative patterns can potentially suppress the abnormal or unhealthy expression of genes associated with diseased or degenerative conditions. By suppressing adverse gene expression, unhealthy (degenerative or disease conditions) may potentially be suppressed or reversed. By stimulating favorable gene expression, healthy conditions can be promoted.

This wearable device may also be referred to herein and in any references incorporated by reference as "wearable device," "device," "portable wearable device," or the like). The wearable device may be described in general as a flat, flexible, and portable device that is designed to be worn relatively continuously by a person. The wearable device may have modalities with tunable parameters. The wearable device may have the ability to optimize the parameters and mixes among such modalities. This functionality, combined with biometric feedback data, and further combined with Artificial Intelligent analytic capabilities, may facilitate the identification and characterization of DNA Resonant frequencies, and the identification of associated "stimulus-response" modeling associated with such biological interactions. For example, this unique and novel combination and application of such capabilities reflected in the present invention may provide unique inputs and guidance to discover the stimulus-response parameters to actively control DNA or gene expression with a prescriptive approach to selectively activate certain positive expressions, and selectively suppress certain negative expressions.

Another aspect of the present invention is a novel method to identify the optimal parameters of the modalities that most effectively achieve a desired result or outcome. The method may consider physiological, biometric, contextual, personal, and population-level genomic data, and may use Artificial Intelligent analytic capabilities to facilitate the identification and characterization of DNA Resonant frequencies, and to identify associated "stimulus-response" modeling associated with such biological interactions. The method will provide unique inputs and guidance to discover the input-output parameters to actively control DNA/gene expression with a prescriptive approach to optimize and personalize a user's treatment and to selectively activate certain positive expressions, and selectively suppress certain negative expressions.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, where.

DETAILED DESCRIPTION OF THE INVENTION

Figure 1:
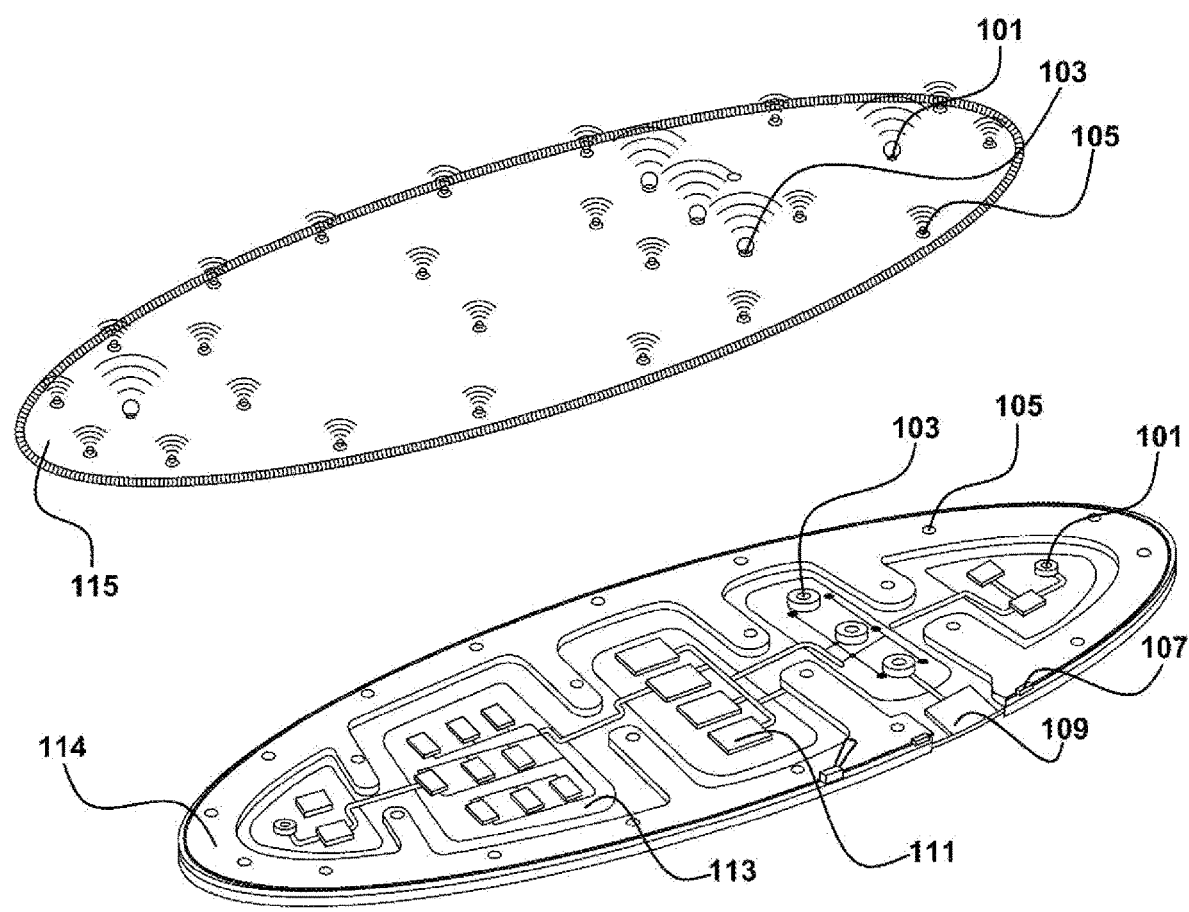
FIG. 1 illustrates one embodiment of the electrical and functional components of the invention. The first layer is shown on the bottom and the second layer is shown on the top.
Figure 2:
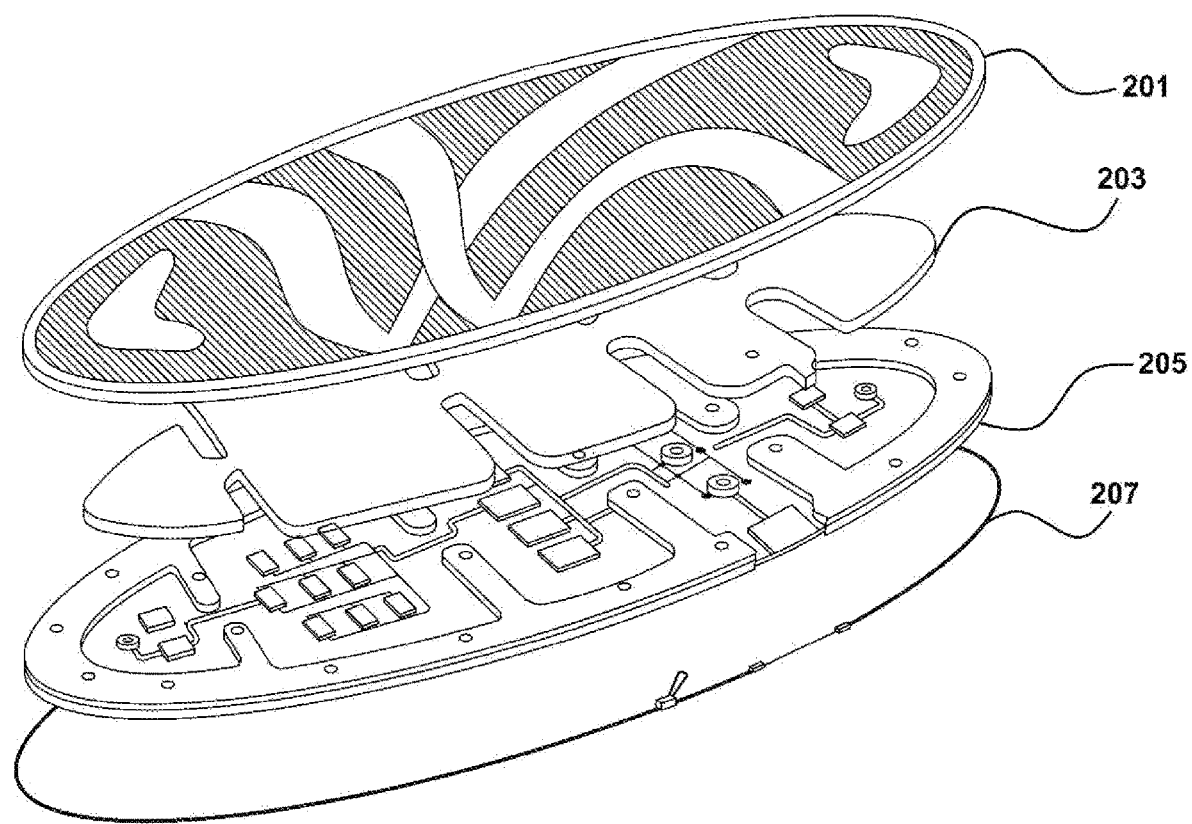
FIG. 2 illustrates one embodiment of the layered construction of the invention. The fourth layer is shown on the top and the first layer is shown on the bottom.

The terminology used herein is for the purpose of describing particular embodiments only and is not intended to be limiting of the invention. The terms "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning in the context of relevant art and the present disclosure will not be interpreted in an idealized or overly formal sense unless expressly so defined herein.

In describing the invention, it will be understood that a number of elements are disclosed. Each of these elements has an individual benefit, and each can also be used in conjunction with one or more, or in some cases all, of the other disclosed elements. Accordingly, for the sake of clarity, this description will refrain from repeating every possible combination of elements in an unnecessary fashion. Nevertheless, the specification and claims should be read with the understanding that such combinations are entirely within the scope of the invention and the claim.

It is to be understood that the concepts or methods discussed herein may be embodied in stand-alone wearable devices as well as, when appropriate, wearable devices that can connect to and use the functionality of external devices. Furthermore, the wearable device may be used on a stand-alone basis or in concert with other external devices, products, and technologies that provide biometric feedback signals including, but not limited to heart rate, blood pressure, temperature, breathing rate, and the like, and contextual data including, but not limited to, positional, velocity, altitude, and activity level data.

It is to be understood that the components of the wearable device discussed herein may be attached, affixed, or connected to each other in any combination through a number of mechanical or chemical means including, but not limited to, stitching, screws, nails, clamps, wires, and the like as well as glues, binding agents, polymers, and the like. The components of the wearable device may be attached, affixed, or connected to each other in any combination that does not inhibit the flexibility, portability, or other functionalities of the wearable device.

It is to be understood that the term "modality" includes any and all methods of interacting with DNA molecules and other biological tissues in a way which may affect or alter a state and/or stimulate or induce any form of response in the DNA or other biological tissues.

It is to be understood that the term "engage" is defined as using modalities to illuminate or otherwise interact with a treatment area in any way that affects DNA molecules and other biological tissues.

It is to be understood that the terms "physiological sensor" or "biometric sensor" is defined as any type of sensor that may sense and collect physiological or biometric data including, but not limited to, impedance, perspiration, vibration, resting pulse rate, post-activity recovery pulse rate and pattern, body temperature, blood pressure, electrical or electromagnetic emissions, heart rate, blood pressure, measurements via electrodes in the 100-2000 MHz range, breathing rate, respiration, secretion, salivation, EKG, EEG, optical and NIR light absorption and scattering, sound, activity level, and sleep data.

It is to be understood that the term "contextual sensor" is defined as any type of sensor that may sense and collect contextual data including, but not limited to, activity level, weather, time of day, movement, location, acceleration, subjective mood state, feeling state, user behaviors, drug use, food and beverage consumption, or exercise pattern data.

In the preferred embodiment of the wearable device, the wearable device may comprise three modalities including micro-mmW emitters 101, magnetic pulse generators 103, and micro-LED emitters 105. The wearable device may further comprise a zipper 107, a USB-C port 109, a programmable control module 111, and a battery pack 113. The wearable device may further comprise a non-conductive material to house its electronic components 114 and optical frequency emitters that are located on a layer of a printed micro-LED mesh 115.

In the preferred embodiment of the wearable device, the wearable device may comprise four layers, wherein the fourth layer 201 may be a decorative cover, wherein the third layer 203 may be a flexible silicon layer, wherein the second layer 205 may be a non-conductive material, and wherein the first layer 207 may be a translucent micro-fiber fabric.

In the preferred embodiment of the wearable device, the wearable device may be attached to a host material and contoured around treatment areas such as knees, lower backs, ankles, and wrists as illustrated in FIG. 3B, FIG. 3C, FIG. 3D, and FIG. 3E.

In the preferred embodiment of the wearable device, the wearable device may comprise an embedded sensor 403, wherein this sensor may be a physiological, biometric, or contextual sensor. The wearable device may be connected to a host material that comprises embedded sensors 401, 402, 404, 405, wherein these sensors may be physiological, biometric, or contextual sensors. The sensors on the wearable device and host material may transmit any collected data to an integrated companion mobile application 501 on an external device.

Figure 6:
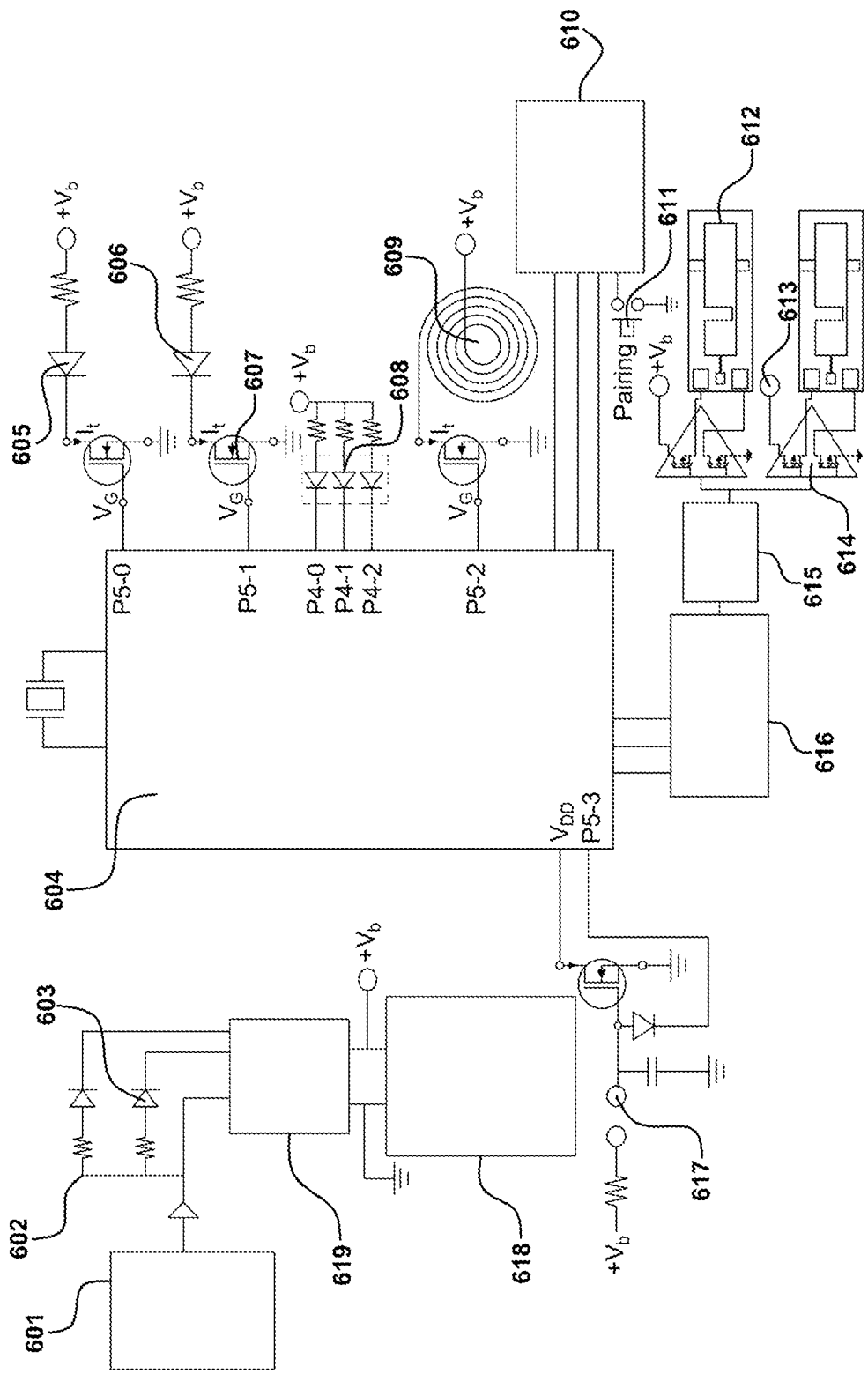
FIG. 6. Illustrates one embodiment of the invention's electrical circuitry.
Figure 7:
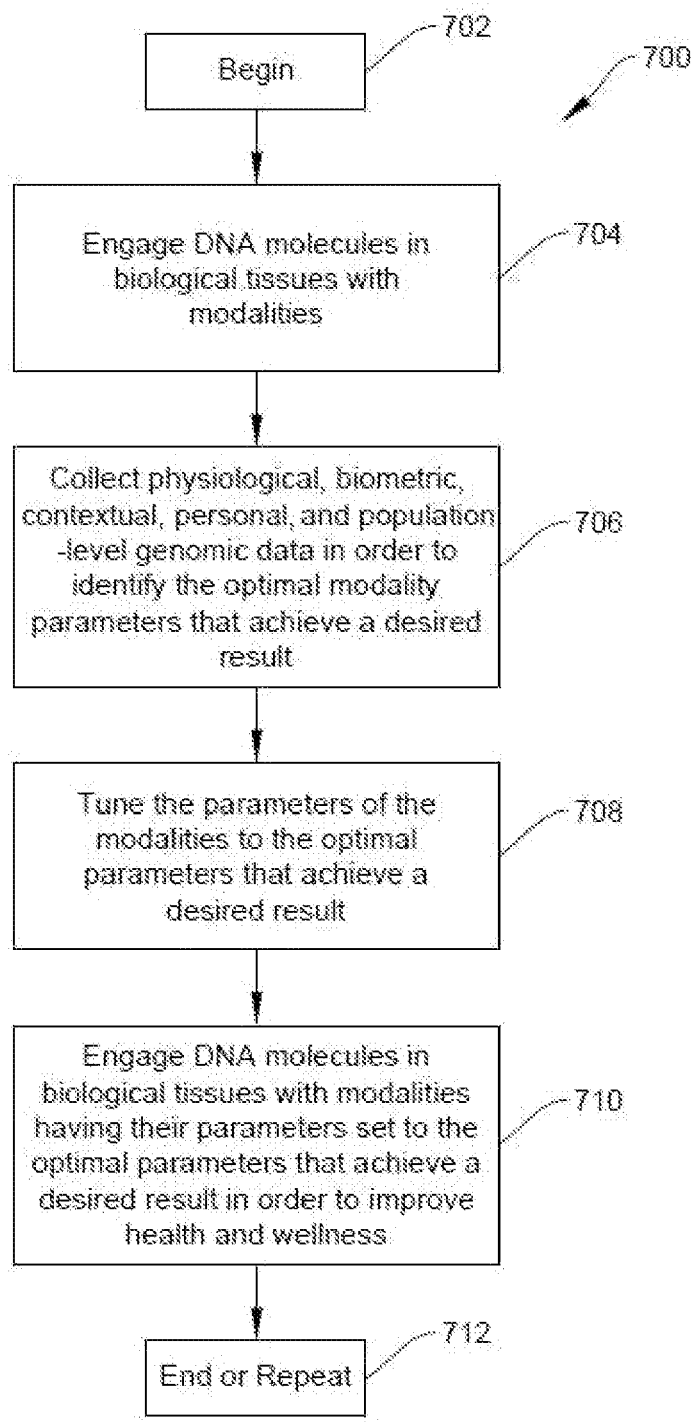
FIG. 7. Illustrates one embodiment of the invention's method.

In the preferred embodiment of the wearable device, the wearable device's circuitry may include the electronics illustrated in FIG. 6. This circuitry may be powered by an external power supply 601 of 5 volts at 1 amp. This power supply may be connected to two resistors 602 and a TP4056 lithium-ion charger. Between the resistors and the TP4056 lithium-ion charger may be two LEDs 603, each LED connected to a resistor and the TP4056 lithium-ion charger. The TP4056 lithium-ion charger is connected to two HCP603450 Honcel batteries, the Honcel batteries being able to output 3.7V and storing 1 Ah of energy. The wearable device's circuitry is controlled by a MSP430FR2355TDBTR microcontroller 604. The microcontroller is connected to a 660 nm LED array 605 and to 850 nm 1 W LED array 606, through transistors 607. The microcontroller is further connected to RGB 5050 SMT LEDs 608 and, through a transistor, to a magnetic pulse PCB coil 609. The microcontroller is further connected to a CC2650MODA Bluetooth LE Module 610 with an antenna. The antenna is connected to a pairing 611. This wearable device's circuit includes two mmW emitters 612. This wearable device's circuit includes a 40 GHz chip antenna. 613. These emitters and antenna are connected to driver amps 614. These driver amps are connected to a Tripler 615. This Tripler is connected to a LMX2492-Q1 14 GHz PLL 616. This PLL is connected to the microcontroller. This microcontroller is connected to a touch-on switch 617. The entire circuit may be powered by two HCP603450 Honcel batteries 618. These batteries may be connected to the TP4056 lithium-ion charger 619. All of aforementioned electrical components of the wearable device as illustrated in FIG. 6. may be connected through wiring or other conductive materials, wherein the wiring or other conductive material may contain resistors, transistors, and any other necessary electrical components in order to retain proper functionality.

In the preferred embodiment of the method 700, the method may comprise beginning 702 through manual user interaction with the wearable device, an external device, or an integrated companion mobile application on an external device or automatically as a decision of an intelligent process or artificial intelligence. This method may further comprise engaging DNA molecules or other biological tissues with a variable combination of modalities 704. This method may further comprise the collection of biometric, contextual, environmental, or personal (subjective user provided or entered data) data feedback and/or input data or information 706. This method may further comprise identifying the optimal frequencies and other such signal parameters which promote most effective outcomes 708. This method may further comprise engaging the treatment areas using the wearable device, the wearable device having the parameters of the modalities set to the optimal parameters in order to achieve the desired result 710. This method may be ended or repeated 712.

Wearable Device:

The wearable device may comprise a first layer 207 meant to be placed flush to skin or clothing. Clothing refers to any suitable covering on a patient's body to which the wearable device may be coupled or attached. The article of clothing may thus form an intermediate layer between the device and the treatment area and may be used to indirectly couple the wearable device to the treatment area. This first layer may also be referred to herein and in any references incorporated by reference as the "skin side," "skin side layer," "translucent microfiber fabric layer" and the like. This first layer 207 may be elliptical in shape and may have a length of 11" and a width of 4.5". This first layer may have a zipper 107 running around its circumference for portability and the first layer may be designed to maximize the passage of the modalities from the wearable device into the treatment area. As such, the first layer 207 may be composed of a translucent microfiber fabric. This translucent microfiber fabric may be designed to maximize pass-through of the modalities into the target treatment area, to provide high levels of comfort when in contact with treatment area surfaces or skin, and to enable ease of cleaning and maintenance by simply wiping with cleaning wipes or moistened towelettes.

The wearable device may further comprise a second layer 205 affixed atop of the first layer 207. This second layer may have the same shape as the first layer and may house the electronic components in a cavity or cavities located within the second layer. The components in the second layer 205 may be intentionally small, flat, and distributed horizontally with ample spacing between components, the ample spacing being large enough to facilitate the flexibility and other functionality of the wearable device. In this preferred embodiment, the electrical connections between components may be designed as "pig-tail" wiring or a flexible or elastic conductive material. The size, shape, spacing, and wiring characteristics of the wearable device may be designed to provide a high degree of flexibility to comfortably bend the device around the contours of various treatment areas.

The wearable device may further comprise a third layer 203 affixed atop of the second layer 205. This third layer may also be referred to herein and in any references incorporated by reference as the "elastic silicon filler," "elastic filler layer," "elastic silicon layer," and the like. This third layer 203 may have the same shape as the first layer 207 and may serve to secure the various components and wiring of the wearable device in place, protecting them from the elements, humidity, shocks, drops, and the like, while facilitating the flexibility needed, via the elastic properties of material, to comfortably wrap around the contours of various treatment areas.

The wearable device may further comprise a fourth layer 201 affixed atop of the third layer 203. This fourth layer may also be referred to herein and in any references incorporated by reference as the "air side," "air side layer," "customizable decorative cover," "decorative cover layer," and the like. This fourth layer may have the same shape as the first layer 207 and may secure all of the wearable device's components in place, provide a decorative outer surface, and further protect the device from external elements. The decorative cover may be designed with arbitrary styling, and is intended to be interchangeable and customizable.

The wearable device's fourth layer 201 may comprise an inner side, the inner side facing the skin and having a reflective surface in order to contain or reflect the modalities back toward the treatment areas in order to maximize the absorption of the modalities into the targeted treatment areas in order to improve overall effectiveness, maximize the efficiency of modality generation with minimum losses in order to allow for reduced power usage through reduced modality requirements, which in turn enables longer operating durations, which in turn enables the use of smaller, more efficient batteries, which in turn minimizes the propagation of ambient radiation, which in turn minimizes or eliminates the potential for any electromagnetic interference caused by the wearable device, which in turn enables the wearable device to be worn for extended periods and in unlimited situational contexts without restriction based on meeting FCC and FDA regulatory guidelines.

The wearable device may further comprise physiological or biometric sensors. These physiological and biometric sensors may include temperature, heart rate, and blood pressure sensors. These physiological and biometric sensors may be embedded in the first layer 207, the second layer 205, or on the outside of the wearable device in any position that enables the physiological and biometric sensors and the wearable device to retain their functionalities. The physiological and biometric sensors may be connected, wired or wirelessly, to the battery pack and the programmable control module.

The wearable device may further comprise a battery pack 113, the battery pack consisting of multiple relatively small batteries connected in a grid pattern. This battery pack 113 may be embedded in the second layer 205 in any position that enables the battery pack and the wearable device to retain their functionalities. This battery arrangement enables flexibility of the device and it is necessary in order for the surface of the wearable device to be flexible enough to bend and flex as it lays flat or curved adjacent to the contours of a treatment area (e.g., wrapping around a knee, elbow, and the like).

The wearable device may further comprise a programmable control module 111. This programmable control module may also be referred to herein and in any references incorporated by reference as "control and communications modules," "control & Bluetooth," "control unit," or the like. This programmable control module may be embedded in the second layer 205 in any position that enables the programmable control module and the wearable device to retain their functionalities. This programmable control module 111 may include a microprocessor with programmable logic to control various device and component parameters, including activation and deactivation of components (turning components on and off), controlling the amplitude or intensity of the modality components (in this manifestation of the device this includes the amplitude of optical micro-LEDs, micro-mmW emitters, and magnetic pulse generator); and controlling communications between and among components and third-party (separate or external) devices, including the integrated companion mobile application 501 and other external and peripheral devices like watches, biometric sensors, GPS location sensors, databases, and the like. The programmable control module may further comprise a Bluetooth communications component that enables communications between the device and external devices, sensors, databases, or the integrated companion mobile application for the exchange of functional commands including on/off, power settings, adjustments to the parameters of modalities, setting of treatment durations, and the like, and for the exchange of data between the device and an integrated companion mobile application, the data including wearable device settings, status, durations, and the like.

The wearable device may further comprise a universal communications and power port, the universal communications and power port may also be referred to herein and in any references incorporated by reference as "USB-C® & Power Ports," and the like. This universal communications and power port may be embedded in the second layer 205 in any position that enables the universal communications and power port and the wearable device to retain their functionalities. This universal communications and power port may allow a standards-based micro USB chord to be inserted in order to enable the charging of the battery pack 113 (when connected to a power source), and for wired communications between the device and other devices, sensors, databases, peripherals, or accessories, including the companion mobile application (such communications can also be done wirelessly using the wireless communication functionality of the programmable control module, including through Bluetooth and the like). This universal communications and power port may be a USB-C® port 109 that allows wired charging and communication between the wearable device and external sensors or devices.

Figure 3A:
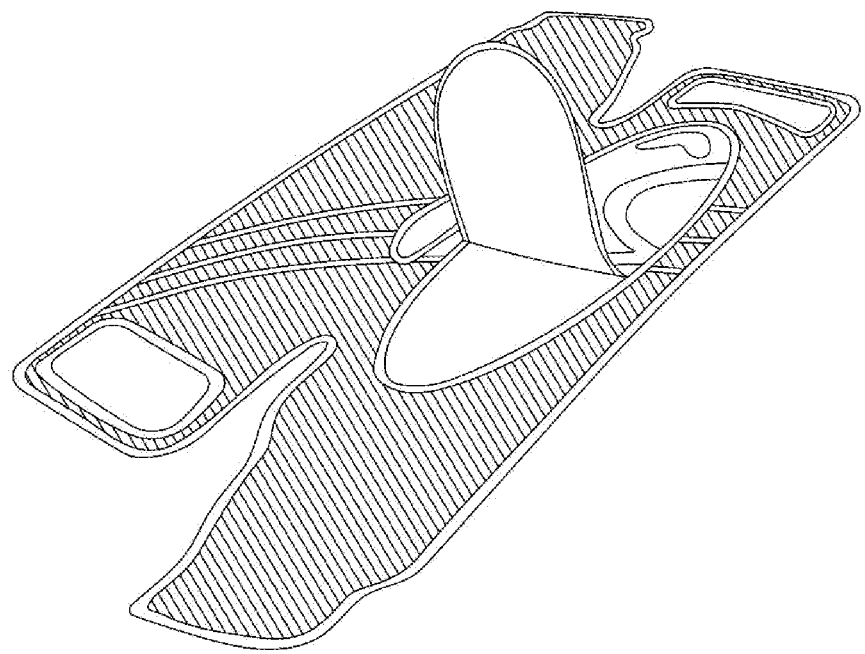
FIG. 3A illustrates one embodiment of the invention's single-SKU design that enables it to be portable or interchangeable onto a variety of host bands.
Figure 3B:
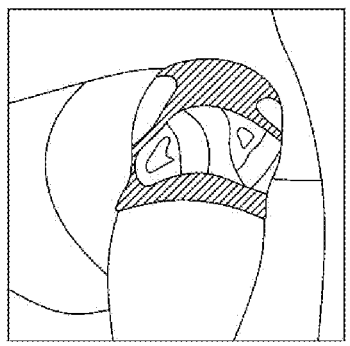
FIG. 3B illustrates one embodiment of the invention where it is attached to a host band and contoured to a user's knee.
Figure 3C:
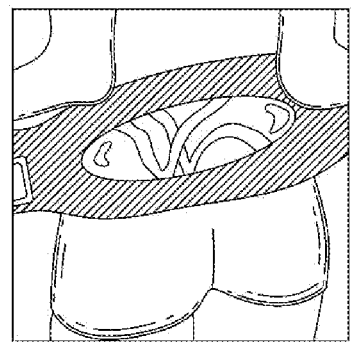
FIG. 3C illustrates one embodiment of the invention where it is attached to a host band and contoured to a user's back.
Figure 3D:
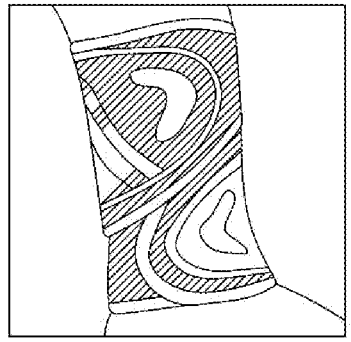
FIG. 3D illustrates one embodiment of the invention where it is attached to a host band and contoured to a user's leg.
Figure 3E:
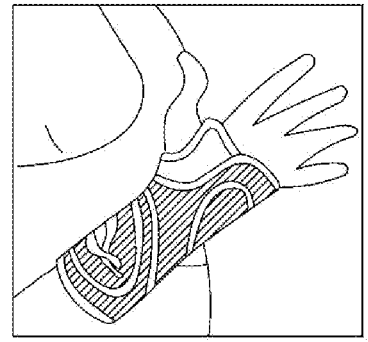
FIG. 3E illustrates one embodiment of the invention where it is attached to a host band and contoured to a user's wrist.
Figure 4:
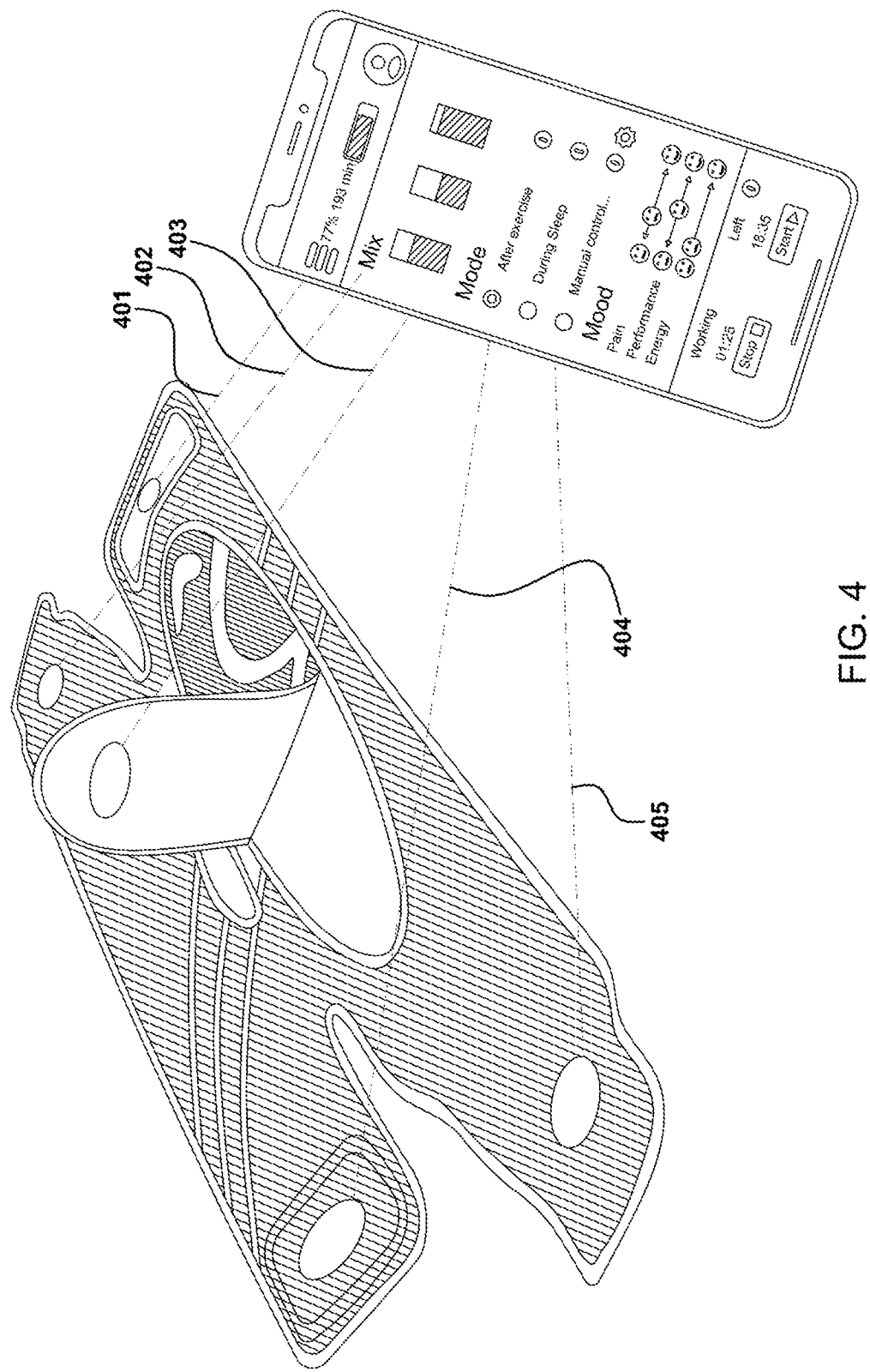
FIG. 4 illustrates one embodiment of the invention where sensors are embedded in the wearable device and host band.
Figure 5:
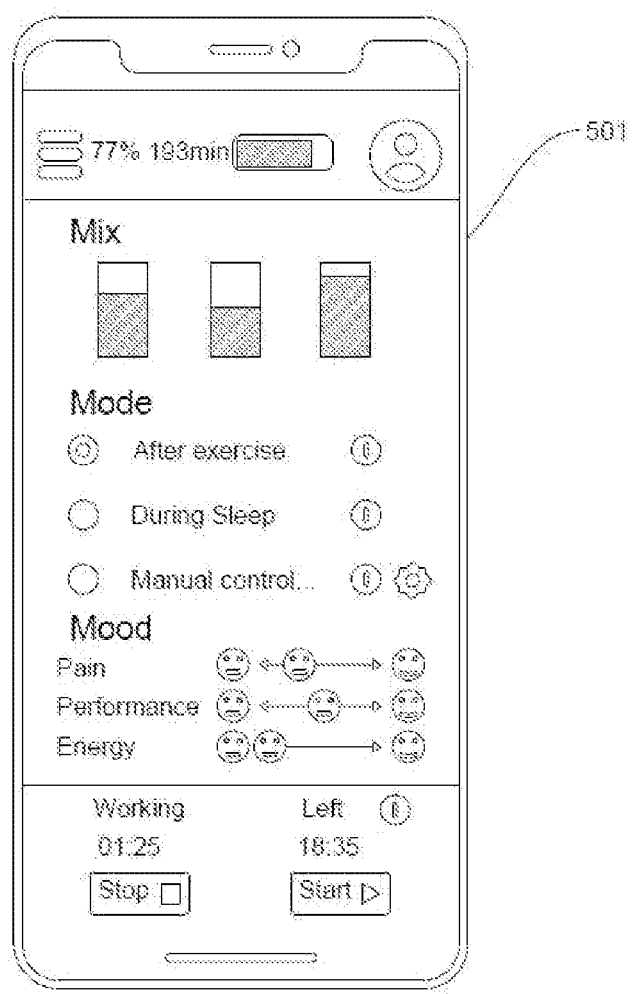
FIG. 5 illustrates one embodiment of the invention where an integrated companion mobile application facilitates user interaction with the invention.

The wearable device may further comprise a zipper attachment 107. The zipper may run around the outer perimeter of the device and may serve to allow the device to be attached to, and detached from, a host material such as a fitness wrap or band as illustrated in FIG. 3A. This may allow the wearable device to be portable or interchangeable between and among a variety of such host materials. One band configuration may be most suitable for fixing the device to a knee, and another for the ankle, and yet another for the elbow, lower back, neck, head, wrist, and the like.

The wearable device may further comprise a printed mesh 115 embedded with Micro-LED light emitters 105. The optical frequencies may be emitted via a printed micro-LED mesh consisting of 24 LED's that are directional and oriented toward the skin-side surface of the device. This printed mesh 115 embedded with micro-LED light emitters 105 may have the same shape as the first layer 207 and may be affixed anywhere between the first and second layer 205 in any position that enables the printed micro-LED mesh 115 and the wearable device to retain their functionalities. The power level and intensity of the micro-LEDs may be controllable via the programmable control module described above. In other embodiments of the wearable device, the precise configuration, type, and number of LEDs can be varied.

The wearable device may further comprise magnetic pulse generators. The magnetic pulse generators may also be referred to herein and in any references incorporated by reference as a "magnetic pulse generator," and the like. FIG. 1. illustrates the preferred positioning of magnetic pulse generators 103. These magnetic pulse generators may comprise three coils connected to a signal generator, controlled by the programmable control module, and powered by the battery pack.

The wearable device may further comprise electromagnetic wave emitters. The electromagnetic wave emitters may also be referred to herein and in any references incorporated by reference as a "em wave emitter," and the like. These electromagnetic wave emitters may be affixed anywhere in the second layer 205 in any position that enables the electromagnetic wave emitters and the wearable device to retain their functionalities. In this preferred embodiment, the electromagnetic wave emitters may be two micro-mmW emitters 101. These electromagnetic wave emitters may be controlled by the control unit and powered by the battery array.

The wearable device may be used on various treatment areas, wherein the treatment areas include, but are not limited to, knees, lower backs, ankles, and wrists as illustrated in FIG. 3B, FIG. 3C, FIG. 3D, and FIG. 3E. Treatment areas may further include elbows, necks, heads, thighs, calves, or any combination thereof.

The desired result or outcome may be to stimulate positive (and mitigate negative) DNA gene expression and other biological processes, wherein positive is defined as beneficial for health and wellbeing and negative is defined as detrimental for health and wellbeing. This wearable device may gently and safely engage biological tissues with low levels of various energies to stimulate positive gene expression in order to promote accelerated healing, pain relief, and performance enhancement through the generation of healthy tissue cells and the suppression of abnormal or unhealthy expression of genes associated with diseased or degenerative conditions. By suppressing adverse gene expression, unhealthy (degenerative or disease conditions) may potentially be suppressed or reversed. By stimulating favorable gene expression, healthy conditions may be promoted. This wearable device may engage DNA molecules, causing DNA molecules to be activated or deactivated, and potentially caused to resonate which further affects such phenomena. This wearable device may be used to engage DNA molecules and other biological tissues in the muscles, ligaments, joints, and the like. This wearable device may engage DNA molecules or other biological tissues with a variable combination of modalities, including Micro-LED light, magnetic pulse, and electromagnetic wave emitters.

The modalities of the wearable device may be orchestrated or coordinated via electronic control to enable a large variety of coordinated patterns, including pulsing, phasing, sequences, waveforms, pulse patterns, pulse shapes, and other such defining attributes of such patterns in limitless combinations of alternating or synchronous patterns.

The wearable device may be enabled to coordinate such treatment modalities and theoretically limitless patterns between and among a number of such devices which may be affixed to two or more treatment areas so as to achieve a desired effect or outcome, and to explore various output or resultant measurements in relation to various input patterns as a way to discover input-output causalities.

The wearable devices may be attached to one, two, or more treatment areas to achieve the desired result or outcome or to facilitate the exploration of various output or resultant measurements in relation to various modality parameter inputs as a way to discover stimulus-response causalities. As illustrated in FIG. 3B, FIG. 3C, FIG. 3D, and FIG. 3E, this wearable device may be attached to a host material that is fastened to various body parts including knees, lower backs, ankles, and wrists. The wearable device may be further used on elbows, necks, heads, thighs, calves, or any combination thereof.

Various modality parameters (frequency, amplitude and the like) may be swept across during the engagement of DNA molecules or other biological tissues (where frequencies used in each mode can be swept across a range of frequencies, amplitudes, waveforms or patterns and the like) to facilitate periodic engagement of DNA molecules and other biological tissues with resonant frequencies to promote activation and deactivation of gene expressions; and where the resultant outcomes may be detectable via various biometric feedback signals (temperature, breathing rate, heart rate and the like). These biometric feedback signals may be used to help identify input-output relationships between such input parameters (frequencies, amplitudes and the like), and also to help identify optimal frequencies and other such signal parameters which promote most effective outcomes;

The wearable device may have a single SKU design, wherein the single SKU design has a surface area and geometry specifically designed to facilitate effective treatment in a maximum number of treatment areas (interchangeable among various treatment areas), and wherein the single SKU design's patterns, amplitudes, and the placement of the three modalities may be specifically designed to optimize effective tissue absorption in order to maximize treatment effectiveness.

The wearable device's modalities may have tunable parameters, including, but not limited to, the activation states, frequencies, amplitudes, waveforms, wavelengths, pulse patterns, periodicities, durations, repetition rates, geometric orientations, and coverage areas.

In one embodiment of the wearable device, the wearable device's patterns, including pulsing, phasing, sequences, wave forms, pulse patterns, pulse shapes, and other such defining attributes of such patterns, may be defined by centralized activity under management by a specified authority or by distributed action as determined by one or more independent users or individuals who may specify such patterns.

In one embodiment of the wearable device, the wearable device may be controlled via a single, multi-modal device with common control, communications, and analytic processing elements that permits cohesive and orchestrated treatment modalities. These multi-modal devices include, but are not limited to, smart-phones with integrated companion mobile applications 501, smart-watches, remote controls, and computers.

In one embodiment of the wearable device, the wearable device may vary a range of voltages between two or more sensors embedded in the device and/or the host materials for the purposes of detecting various measurements, including bioimpedance, moisture levels, electrolytes, dielectrics, temperatures, and the like.

In one embodiment of the wearable device, the wearable device's feedback signals and/or physiological, biometric, or contextual feedback data may include electric and electronic signals and properties; EKG, EEG, bioimpedance measurements (via electrodes), measurements via electrodes in the 100-2000 MHz range, temperature, perspiration, optical and NIR light absorption and scattering measurements, sound measurements, acceleration, subjective mood states, feeling states, and other discernible sensations of a user, as well as user behaviors such as drug use, food and beverage consumption, exercise patterns, sleep patterns, respiration, secretion, and other such feedback, physiological, biometric, or contextual data;

In one embodiment of the wearable device, the modalities may further include light emitters, optical frequency emitters, near-infrared light emitters, heat emitters, mechanical vibration motors, voltage or current emitters, acoustic emitters, static field emitters, micro-mmW emitters, electronic stimulation emitters, eclectic voltage or current emitters, optical emitters, oscillating or static electric fields via an insulator or fabric, and the like, in order to affect gene expression and other cellular activities to promote healthy generative or regenerative and mitigate degenerative conditions. These modalities may be embedded in the second layer 205 in any position that enables the modalities and the wearable device to retain their functionalities.

In one embodiment of the wearable device, the physiological or biometric sensors may further include impedance, perspiration, vibration, resting pulse rate, post-activity recovery pulse rate and pattern, electrical or electromagnetic emissions, breathing rate, respiration, secretion, salivation, EKG, EEG, optical and NIR light absorption and scattering, sound, and sleep sensors. These physiological and biometric sensors may be embedded in the first layer 207, the second layer 205, or on the outside of the wearable device in any position that enables the physiological and biometric sensors and the wearable device to retain their functionalities. The physiological and biometric sensors may be connected, through wires or other conductive materials, to the battery pack 113 and the programmable control module 111.

In one embodiment of the wearable device, the zipper 107 may be replaced with fasteners including straps, snaps, hook and loop fixtures, and the like while retaining the wearable devices' portability and interchangeability. These fasteners may be separate or separable from the wearable device in order to enable the wearable device, without fasteners, to attach to a host material that can hold the wearable device, without fasteners, in place. These fasteners may be used to fasten the wearable device to or within articles of clothing and worn as a functional fashion accessory. This wearable device may be attached to or embedded in a broad range of form factors, including hats, gloves, slippers, head bands, car seats, pillow cases, blankets, socks, shoes, facial masks, and the like using these fasteners.

In one embodiment, the wearable device may connect to an external device, peripheral, or accessory, e.g. a GPS receiver in a smartphone. This wearable device may communicate with the external devices, peripherals, or accessories using standard wired or wireless communications connections. The concepts disclosed and discussed herein may be applied to both stand-alone wearable devices as well as wearable devices that connect with and use the sensors or other functionalities of external devices, peripherals, or accessories e.g., movement tracking data provided by a smartphone, GPS, and the like.

In one embodiment of the wearable device, the programmable control module 111 may contain a processor that may be controlled by computer-executable instructions stored in memory so as to provide functionality such as is described herein. In other embodiments, such functionality may be provided in the form of an electrical circuit. In yet other embodiments, such functionality may be provided by a processor or processors controlled by computer-executable instructions stored in a memory coupled with one or more specially-designed electrical circuits.

In one embodiment of the wearable device, the wearable device's battery pack 113 may be fully enclosed in the body of the wearable device, wherein the battery pack has the ability to be charged through inductive charging, enabling the wearable device to be entirely free of any openings for plugs or wire passages.

In one embodiment of the wearable device, the wearable device may be entirely sealed within Silicone or similar such flexible materials including, but not limited to, nylon and rubber. The silicone or similar such flexible materials will permit the wearable device to be worn in a broad range of environmental contexts including in a swimming pool, exposed to the elements, while showering, bathing, or swimming.

In one embodiment of the wearable device, the wearable device may include contextual sensors, wherein the contextual sensors include, but are not limited to, activity level, weather, time of day, movement, location, acceleration, subjective mood state, feeling state, user behavior, drug use, food and beverage consumption, or exercise pattern sensors. These contextual sensors may sense and collect contextual data including, but not limited to activity level, weather, time of day, movement, location, acceleration, subjective mood state, feeling state, user behavior, drug use, food and beverage consumption, or exercise pattern data. These contextual sensors may be embedded in the first layer 207, the second layer 205, or on the outside of the wearable device in any position that enables the contextual sensors and the wearable device to retain their functionalities. The contextual sensors are connected, through wires or other conductive materials, to the battery pack 113 and the programmable control module 111.

In one embodiment of the wearable device, the wearable device may have optical frequency emitters that are located on a layer of a printed micro-LED mesh 115 consisting of 24 LEDs that are directional and oriented toward the skin-side surface of the wearable device, the mesh being attached, through mechanical or chemical means, anywhere between the first and fourth layer 201 of the wearable device.

Method:

It is to be understood that while the method 700 included herein is presented in the context of a wearable device, this method may also be applied in other contexts as well if the appropriate hardware is available. E.g., many external devices such as smartphones include motion sensors, such as accelerometers, and the method discussed herein may, if appropriate hardware is available in the external device, be embodied using that external device. In effect, this may be viewed as turning a smartphone into some form of an external device in order to gather data for the purposes of stimulating positive DNA gene expression and other positive biological processes. Such embodiments are also to be understood to be within the scope of this disclosure.

The desired result or outcome may be to stimulate positive (and mitigate negative) DNA gene expression and other biological processes, wherein positive is defined as beneficial for health and wellbeing and negative is defined as detrimental for health and wellbeing. This method may use a wearable device to gently and safely engage biological tissues with low levels of various energies to stimulate positive gene expression as way to promote accelerated healing, pain relief, and performance enhancement through the generation of healthy tissue cells and to suppress abnormal or unhealthy expression of genes associated with diseased or degenerative condition. By suppressing adverse gene expression, unhealthy (degenerative or disease conditions) can potentially be suppressed or reversed. By stimulating favorable gene expression, healthy conditions can be promoted. This method may be used to engage DNA molecules, causing DNA molecules to be activated or deactivated, and potentially caused to resonate which further affects such phenomena. This method can be used to engage DNA molecules and other biological tissues in the muscles, ligaments, joints, and the like. This method can engage DNA molecules or other biological tissues with a variable combination of modalities 704 including LED light emitters, micro-LED light emitters, magnetic pulse generators 103, electromagnetic wave emitters, red light emitters, optical frequency emitters, near-infrared light emitters, heat emitters, mechanical vibration motors, voltage or current emitters, acoustic emitters, static field emitters, micro-mmW emitters 101, electronic stimulation emitters, eclectic voltage or current emitters, and optical emitters.

The method's wearable device may be applied to various treatment areas, wherein the treatment areas include, but are not limited to, knees, lower backs, ankles, wrists, elbows, necks, heads, thighs, calves, or any combination thereof. The steps of this method 700 may begin 702 through manual user interaction with the wearable device, an external device, or an integrated companion mobile application on an external device or automatically as a decision of an intelligent process or artificial intelligence.

The method's wearable device's feedback signals and/or physiological, biometric, or contextual feedback data may include electric and electronic signals and properties; EKG, EEG, bioimpedance measurements (via electrodes), measurements via electrodes in the 100-2000 MHz range, temperature, perspiration, optical and NIR light absorption and scattering measurements, sound measurements, acceleration, subjective mood states, feeling states, and other discernible sensations of a user, user behaviors such as drug use, food and beverage consumption, exercise patterns, sleep patterns, respiration, secretion, and other such feedback, physiological, biometric, or contextual data;

The method's contextual sensors may comprise the contextual sensors of the wearable device, host material, or external device may include activity level, weather, time of day, movement, location, acceleration, subjective mood state, feeling state, user behaviors, drug use, food and beverage consumption, or exercise pattern sensors.

The method's physiological or biometric data may include impedance, perspiration, vibration, resting pulse rate, post-activity recovery pulse rate and pattern, body temperature, blood pressure, electrical or electromagnetic emissions, heart rate, blood pressure, measurements via electrodes in the 100-2000 MHz range, breathing rate, respiration, secretion, salivation, EKG, EEG, optical and NIR light absorption and scattering, sound, activity level, or sleep data.

The method's contextual data may include activity level, weather, time of day, movement, location, acceleration, subjective mood state, feeling state, user behavior, drug use, food and beverage consumption, or exercise pattern data.

The method's personal data may include any data that fully characterize the users' attributes including, but not limited to, genetic predispositions, height, and weight.

The method's population-level genomic data may include, but is not limited to, genetic data from genetic services such as 23AndMe or Ancestry.com.

The method's wearable devices may be attached to one, two, or more treatment areas to achieve the desired result or outcome or to facilitate the exploration of various output or resultant measurements in relation to various modality parameter inputs as a way to discover stimulus-response causalities. This wearable device may be attached to a host material that is fastened to various body parts including knees, lower backs, ankles, wrists, elbows, necks, heads, thighs, calves, or any combination thereof.

The method may comprise the use of an integrated companion mobile application 501 to control the on/off state of the wearable device, wearable device settings, duration, usage modalities, and the like, while also serving as a user interface for interaction with users to collect various user inputs (including usage objectives, contextual information, and the like). This mobile application may also collect biometric feedback signals (like heart rate, temperature, activity level, step counts, blood pressure, breathing rate, and the like) both directly (via mobile device) and through interactions with other external or peripheral devices (like sports watches, and other fitness wearables). This may serve to capture data and insights relating (and correlating) the usage of the device, including frequency and duration of use, power settings (or mix) among the various treatment modalities, and contextual information (like goals, activity type, environmental conditions, subjective user inputs, and the like).

The method may comprise the collection of biometric, contextual, environmental, or personal (subjective user provided or entered data) data feedback and/or input data or information 706. This data collection may provide considerable data to help relate device usage conditions and parameters with outcome-related information (like physiological feedback measures and subject user assessments of mood, feelings, and the like). This may help personalize and optimize device modalities both manually (by providing insights to suggest settings and adjustments for users) and automatically through artificial intelligence agents and services which may help discover and surface patterns and insights to help recommend or automatically set and adjust settings for various usage conditions, objectives, and environmental factors, and the like. These intelligent processes of personalization and optimization may be made possible by the unique features and modalities of the present invention, in combination with an intelligent mobile application making use of precision location technologies, integration with other devices providing biometric data, and artificial intelligence to examine and identify correlations between input factors (device settings, environmental conditions, and the like) and output factors (heart rate, breathing rate, temperature, user feedback and the like).

In one embodiment of the method, DNA molecules and other cellular or biological tissues in the muscles, ligaments, joints, and the like may be engaged with certain frequencies, amplitudes, patterns and the like to stimulate positive and suppress negative gene expression and cellular activity to promote healthy generative or regenerative conditions and mitigate degenerative conditions;

In one embodiment of the method, DNA molecules and other cellular or biological tissues may be engaged with a variable combination of several treatment modalities including magnetic pulse generators 103, micro-mmW emitters 101, and micro-LED emitters 105.

In one embodiment of the method, the method's wearable device's modalities may have tunable parameters, including, but not limited to, the activation states, frequencies, amplitudes, waveforms, wavelengths, pulse patterns, periodicities, durations, repetition rates, geometric orientations, and coverage areas.

In one embodiment of the method, there may an intelligent process on the external device or on the integrated companion mobile application of an external device, wherein the intelligent process, governed by stimulus-response feedback loops, considers the parameters of the modalities and the physiological, biometric, contextual, personal, or population-level genomic data of the user in order to collect stimulus-response feedback data about how the parameters of the modalities affect the user.

In the preferred embodiment of the method, artificial intelligence may analyze and correlate device modalities across a wide range of settings including various modality mixes, intensities, or durations and contextual parameters and discernable physiological and biometric feedback data in order to identify insights, patterns, causality indicators, and to facilitate predictive analytics and prescriptive recommendations to achieve or influence certain desired results or outcomes. This artificial intelligence may include, but is not limited to, AI analytics, machine learning, or pattern identification. This artificial intelligence may further consider the user's physiological, biometric contextual, biometric, personal, or population-level genomic data.

In one embodiment of the method, artificial intelligence, in possible combination with human intelligence and analytics, may examine the physiological, biometric, contextual, personal, or population-level genomic data collected by a population of the wearable device's users' wearable devices, host materials, external devices, or integrated companion mobile applications on an external device, in order to discern population trends, causalities, commonalities, best practices, as well as potential differentiation in stimulus-response patterns among sub-populations within the larger population.

In one embodiment of the method, artificial intelligence, in possible combination with human intelligence and analytics, may be applied to examine the data collected by a population of the wearable device's users' wearable devices, host materials, external devices, or integrated companion mobile applications on an external device, in combination with population-level genomic data, in order to correlate results of using and adjusting the wearable device's parameters, resultant outcomes, and various genetic characteristics in order to identify potential insights or commonalities.

In one embodiment of the method, DNA molecules and other cellular or biological tissues may be engaged with such multiple treatment modalities wherein the relative frequencies, amplitudes, patterns, geometric orientations, coverage areas and the like are tunable in order to achieve a variety of targeted outcomes; and where such tunability can be achieved manually by a user's actions and/or automatically by an intelligent process governed by stimulus-response feedback loops which sense the results given incident parameters, and wherein Artificial Intelligence (including AI analytics, machine learning, pattern identification, and the like) may vary input parameters based on desired output or outcome results (or may recommend input parameters and/or their adjustment based on the same).

In one embodiment of the method, an integrated companion mobile application 501 may activate and control the device, including manual and automated options to adjust the mix of modalities (or combination of setting parameters including intensity or amplitude, waveform, duration, frequencies or wavelengths, and the like to govern the output of the operative modalities). This integrated companion mobile application of an external device or an external device, may allow the user to manually tune the parameters of the modalities of the wearable device.

In one embodiment of the method, the modalities of the wearable device may be orchestrated or coordinated via electronic control to enable a large variety of coordinated patterns, including pulsing, phasing, sequences, waveforms, pulse patterns, pulse shapes, and other such defining attributes of such patterns in limitless combinations of alternating or synchronous patterns.

In one embodiment of the method, the wearable device may be enabled to coordinate such treatment modalities and theoretically limitless patterns between and among a number of such devices which may be affixed to two or more treatment areas so as to achieve a desired effect or outcome, and/or to explore various output or resultant measurements in relation to various input patterns as a way to discover input-output causalities.

In one embodiment of the method, the multi-mode engagement of DNA molecules or other biological or cellular tissues using optical, magnetic pulse, electromagnetic, infrared/heat, and other modalities may be controlled via a single, multi-modal device with common control, communications, and analytic processing elements for cohesive and orchestrated treatment modalities.

In one embodiment of the method, various modality parameters (frequency, amplitude and the like) may be swept across during the engagement of DNA molecules or other biological tissues (where frequencies used in each mode can be swept across a range of frequencies, amplitudes, waveforms or patterns and the like) to facilitate periodic engagement of DNA molecules and other biological tissues with resonant frequencies to promote activation and deactivation of gene expressions; and where the resultant outcomes may be detectable via various biometric feedback signals (temperature, breathing rate, heart rate and the like). These biometric feedback signals may be used to help identify input-output relationships between such input parameters (frequencies, amplitudes and the like), and also to help identify optimal frequencies and other such signal parameters which promote most effective outcomes 708.

In one embodiment of the method, Artificial Intelligence may be used to analyze and correlate device modalities (across a wide range of settings, including mix of modalities, intensities, durations, and the like) and contextual parameters (activity level, movement, location, weather and other environmental signals, and the like) and discernable biometric feedback data (heart rate, breath rate, and the like) to identify insights, patterns, causality indicators, and to facilitate predictive analytics and prescriptive recommendations to achieve or influence certain desired outcomes (to achieve A, take actions B, etc).

In one embodiment of the method, Artificial Intelligence, Machine Learning, and/or human intelligence and analytics may be applied to examine data across a population of device users together with associated device, environmental, and biological data to discern population trends, causalities, commonalities, best practices, and the like, as well as potential differentiation in stimulus-response patterns among sub-populations within the larger population (people like you experience results like this to situational conditions like that, and the like).

In one embodiment of the method, artificial intelligence, machine learning, and human intelligence and analytics may be applied to examine the data generated by the wearable device (input parameters like frequency, amplitude, waveforms and the like, and resultant output parameters, including biometric response data, and contextual data like time of day, altitude, movement and the like) in combination with population-level genomics data (for examples from services like 23AndMe, Ancestry.com, and the like) to correlate results of using and adjusting device parameters, resultant outcomes, and various genetic characteristics in order to identify potential insights, commonalities, and the like.

In one embodiment of the method, the treatment areas may be engaged using the wearable device, the wearable device having the parameters of the modalities set to the optimal parameters in order to achieve the desired result or outcome 710. The steps of this method can be ended or repeated 712.

One embodiment of the method comprises the collection of input parameters like data or analytically derived insights obtained through integration or connectivity to a user's medical records and other such historical information, including a user's dietary regimen, records of activities, schedule-related inputs including travel, hours worked, vacation activities, and so on, as well as biochemical measurements pertaining to perspiration, respiration, salivation, and other metrics, and bioimpedance measurements via electrodes in the wearable device and/or host band.

In one embodiment of the method, the DNA molecules and other biological or cellular tissues may be engaged with a variety of modalities including optical, electromagnetic, magnetic pulse, infrared/heat; audio/sound; static magnetic fields; electrical voltage and current patterns; pulsed, oscillating, or static electric fields via an insulator or fabric; and the like to effect gene expression and other cellular activities to promote healthy generative/regenerative and mitigate degenerative conditions;

In one embodiment of the method, the wearable device may vary a range of voltages between two or more sensors embedded in the device and/or the host band for the purposes of detecting various measurements, including bioimpedance, moisture levels, electrolytes, dielectrics, temperatures, and the like.

In one embodiment of the method, the method may be controlled via a single, multi-modal device with common control, communications, and analytic processing elements that permits cohesive and orchestrated treatment modalities. These multi-modal devices include, but are not limited to, smart-phones, smart-watches, remote controls, and computers.

In one embodiment of the method, the modalities may include LED light emitters, micro-LED light emitters, magnetic pulse generator 103s, electromagnetic wave emitters, red light emitters, optical frequency emitters, near-infrared light emitters, heat emitters, mechanical vibration motors, voltage or current emitters, acoustic emitters, static field emitters, micro-mmW emitters 101, electronic stimulation emitters, eclectic voltage or current emitters, and optical emitters.

In one embodiment of the method, the wearable device's patterns, including pulsing, phasing, sequences, wave forms, pulse patterns, pulse shapes, and other such defining attributes of such patterns, may be defined by centralized activity under management by a specified authority or by distributed action as determined by one or more independent users or individuals who may specify such patterns.

We claim:

1. A wearable device for promoting health and wellness comprising:
   a first layer of translucent or transparent fabric or material, having a flexibility needed to comfortably wrap around a treatment area;
   a zipper running around an outer perimeter of the first layer of the wearable device, wherein said zipper allows the wearable device to be attached to a host material in order to be portable or interchangeable between and among the host materials;
   a second layer of non-conductive material attached atop of the first layer through mechanical or chemical means, wherein said second layer possesses a flexibility needed to comfortably wrap around the treatment area and possesses the capability to have electronic components embedded within the second layer of non-conductive material, wherein the electronic components embedded within the second layer of non-conductive material, comprise a battery pack, a programmable control module, a universal communications and power port, physiological, biometric, and contextual sensors, and modalities;
   wherein the battery pack is embedded in the second layer through mechanical or chemical means;
   wherein the physiological, biometric, and contextual sensors are embedded in the second layer through mechanical or chemical means;
   wherein said physiological, biometric, and contextual sensors are configured to sense and collect a plurality of physiological, biometric, and contextual data including body temperature, heart rate, and blood pressure;
   wherein the modalities are embedded in the second layer through mechanical or chemical means;
   wherein said modalities include micro-LED light emitters, magnetic pulse generators, and micro-mmW emitters, the modalities configured to engage DNA molecules and other biological tissues to accelerate healing, pain relief, and performance enhancement;
   wherein the programmable control module is embedded in the second layer through mechanical or chemical means;
   wherein said programmable control module is configured to tune parameters of the modalities and is configured to allow the wearable device to communicate, through wireless means, with at least one of:
     a physiological, biometric, or contextual sensor of the host material,
     a physiological, biometric, or contextual sensor of an external device,
     the external device,
     an integrated companion mobile application of the external device,
     or a database;
   wherein the universal communications and power port is embedded in the second layer through mechanical or chemical means;
   wherein said universal communications and power port is configured to communicate, through wired means, with a sensor on the host material, a sensor of the external device, the external device, the integrated companion mobile application of the external device, or the database; wherein the conductive component within the second layer, is configured for connecting, in any combination, the battery pack, the programmable control module, the universal communications and power port, the physiological, biometric, and contextual sensors, and the modalities;
   a third layer of elastic silicone attached atop of the second layer through mechanical or chemical means, wherein said third layer possesses a flexibility to comfortably wrap around the treatment area, secures the conductive component and the electronic components in place, and protects the conductive component and the electronic components of the wearable device; and a fourth layer of a decorative covering attached atop of the third layer through mechanical or chemical means;
   wherein said fourth layer possesses a flexibility to comfortably wrap around the treatment area, secures all of the electronic components of the wearable device together, and provides protection against humidity, shock, and drops.

2. The wearable device as in claim 1, wherein the first layer is made of a translucent microfiber material, the translucent microfiber material designed to maximize pass-through of the modalities into the treatment area, provide high levels of comfort when in contact with treatment area surfaces or skin, and enable ease of cleaning and maintenance by simply wiping with cleaning wipes or moistened towelettes.

3. The wearable device as in claim 1, wherein the fourth layer has an inner side, the inner side facing skin and having a reflective surface in order to contain or reflect the modalities back toward the treatment area[s].

4. The wearable device as in claim 1, wherein said wearable device is configured to be controlled via a single, multi-modal device with common control, a communication element, and analytic processing elements that permits cohesive and orchestrated treatment modalities.

5. The wearable device as in claim 1, wherein said wearable device is configured to be fastened to or within articles of clothing and worn as a functional fashion accessory.

6. The wearable device as in claim 1, wherein said micro-LED emitters are located on a layer of a printed micro-LED mesh consisting of 24 LEDs that are directional and oriented toward a skin-side surface of the wearable device.

7. The wearable device as in claim 1, wherein said modalities are configured to be coordinated to enable a variety of coordinated patterns comprising pulsing, phasing, sequences, waveforms, pulse patterns, and pulse shapes.

8. The wearable device as in claim 1, wherein said wearable device is configured to be attached to one, two, or more treatment areas in order to accelerate healing, pain relief, and performance enhancement or to facilitate an exploration of various output or resultant measurements in relation to a variety of parameters of the modalities as a means of discovering stimulus-response causalities.

9. The wearable device as in claim 1, wherein said zipper is configured to be replaced with fasteners selected from a group consisting of straps, snaps, or hook and loop fixtures.

10. The wearable device as in claim 9, wherein said fasteners are separate or separable from the wearable device in order to enable the wearable device, without said fasteners, to attach to the host material that can hold the wearable device in place.

11. The wearable device as in claim 1, wherein said universal communications and power port is a USB-C port that allows wired charging and communication between the wearable device and external sensors or devices.

12. The wearable device as in claim 1, wherein said external device or the integrated companion mobile application of the external device, allows a user to manually tune the parameters of the modalities of the wearable device, and wherein said integrated companion mobile application is configured to activate and control the wearable device, and is further configured to have manual and automated options to tune the parameters of the modalities or to adjust a mix of the modalities.

13. A wearable device for promoting health and wellness comprising:
a first flexible layer of translucent or transparent material configured to wrap around to be flush with a treatment area;
a second flexible layer of non-conductive material attached atop the first layer;
a battery pack;
a plurality of operative modalities positioned on or within the second layer and configured to interact with the treatment area through the first flexible layer, wherein said plurality of operative modalities comprise:
a plurality of red light LED emitters,
a plurality of near-infrared light LED emitters,
at least one magnetic pulse generator, and
at least one mechanical vibration motor,
wherein the plurality of operative modalities are configured for multi-mode engagement with the treatment;
a programmable control module configured to operate and tune the plurality of operative modalities;
a plurality of conductors configured to operatively connect, in any combination, the battery pack, the programmable control module, and the plurality of operative modalities; and
wherein the programmable control module is further configured to operate the plurality of near-infrared light LED emitters, the at least one magnetic pulse generator, and the at least one mechanical vibration motor together with the plurality of red light LED emitters, thereby increasing an efficacy thereof.

14. The wearable device as in claim 13, wherein the plurality of red light LED emitters are configured for illuminating the treatment area to cause activation of gene expressions in DNA molecules.

15. The wearable device as in claim 14, wherein the plurality of red light LED emitters are configured for illuminating the treatment area to cause the DNA molecules to resonate.

16. The wearable device as in claim 13, wherein operating the plurality of near-infrared light LED emitters, the at least one magnetic pulse generator, and the at least one mechanical vibration motor together with operating the plurality of red light LED emitters causes a synergistic effect thereof.

17. The wearable device as in claim 13, further comprising at least one additional operative modality configured to interact with the treatment area and selected from a group consisting of: at least one optical frequency emitter, at least one heat emitter, at least one voltage or electrical current emitter, at least acoustic emitter, and at least one micro-mmW emitter, wherein the programmable control module is configured to operate the plurality of operative modalities of the wearable device at the same time.

18. The wearable device as in claim 13, further comprising at least one sensor positioned on or within the second layer and configured to sense and transmit at least one of a physiological or biometric parameter and a contextual parameter.

19. The wearable device as in claim 18, wherein the at least one physiological or biometric parameter is selected from a group consisting of a temperature, a heart rate, a blood pressure, an EKG, an EEG, a bioimpedance measurement, a perspiration measurement, and a breathing rate.

20. The wearable device as in claim 18, wherein the at least one contextual parameter is selected from a group consisting of an optical or near infra-red light absorption and scattering measurement, a sound measurement, a user movement measurement, an acceleration measurement, an exercise pattern, a sleep pattern, a velocity measurement, a positional parameter, an altitude measurement, and a time of day parameter.

21. The wearable device as in claim 13, further comprising a fastener connected thereto and configured to removably attach the wearable device to a band or a wrap.

22. The wearable device as in claim 13, wherein the programmable control module is further configured to allow the wearable device to communicate with an external device.

* * * * *